US006645911B2

(12) United States Patent
Baltruschat et al.

(10) Patent No.: US 6,645,911 B2
(45) Date of Patent: Nov. 11, 2003

(54) SYNERGISTIC HERBICIDAL MIXTURES

(75) Inventors: Helmut Baltruschat, Schweppenhausen (DE); Astrid Brandt, Mainz (DE); Herve Vantieghem, Basking Ridge, NJ (US); Wessel Nuyken, Otterstadt (DE); Michael Vonend, Bad Duerkheim (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/825,694

(22) Filed: Apr. 4, 2001

(65) Prior Publication Data

US 2002/0028747 A1 Mar. 7, 2002

Related U.S. Application Data

(60) Provisional application No. 60/231,631, filed on Sep. 11, 2000, and provisional application No. 60/194,383, filed on Apr. 4, 2000.

(51) Int. Cl.$^7$ .................. A01N 43/36; A01N 43/40; A01N 43/653; A01N 43/824
(52) U.S. Cl. .................. 504/130; 504/138; 504/139
(58) Field of Search .............. 504/130, 138, 504/139

(56) References Cited

U.S. PATENT DOCUMENTS

| | | | | |
|---|---|---|---|---|
| 5,062,884 A | | 11/1991 | Plath et al. ............ | 71/95 |
| 5,090,991 A | * | 2/1992 | Forster et al. ............ | 71/90 |
| 5,237,089 A | | 8/1993 | Plath et al. ............ | 560/15 |
| 5,294,597 A | * | 3/1994 | Foster et al. ............ | 504/255 |
| 5,674,807 A | * | 10/1997 | Baltruschat ............ | 504/130 |
| 5,859,920 A | * | 1/1999 | Dahmen et al. ............ | 504/103 |
| 5,935,905 A | | 8/1999 | Mito ............ | 504/128 |
| 6,030,924 A | * | 2/2000 | Mayer et al. ............ | 504/116 |
| 6,054,410 A | | 4/2000 | Landes et al. ............ | 504/134 |
| 2003/0022792 A1 | * | 1/2003 | Hacker et al. ............ | 504/127 |

FOREIGN PATENT DOCUMENTS

| | | | |
|---|---|---|---|
| CA | 2340193 | | 8/1999 |
| CA | 2340241 | | 8/1999 |
| DE | 196 33 271 | * | 2/1998 |
| EP | 937397 | | 8/1999 |
| WO | 97/10714 | | 3/1997 |
| WO | 00/08932 | | 2/2000 |
| WO | 01/22819 | | 4/2001 |
| WO | 01/35740 | | 5/2002 |

OTHER PUBLICATIONS

White et al., AC900001: A new herbicide for broadleaf weed control in cereals, The 1999 Brighton Conference –Weeds, vol. 1, 1999, pp. 47–52 (XP000989500, p. 52, paragraph 2).
Cauchy, P., "Carfentrazone–ethyl. Cereal herbicide," retrieved from STN–International, accession no. 2001:12464 CABA (XP002190646 abstract), Oct. 2000, pp. 55–58.
Grossmann et al., Protoporphyrinogen oxidase–inhibiting activity of the new, wheat–selective isoindoldione herbicide, cinidon–ethyl, Pesticide Science, 1999, pp. 687–695.
Van Saun et al, Proc. Br. Crop. Prot. Conf., Weeds, 1993, pp. 19–22.
S.R. Colby, Calculating Synergistic and Antagonistic Responses of Herbicide Combinations, Weeds, 1967, pp. 20–22.

* cited by examiner

*Primary Examiner*—S. Mark Clardy
(74) *Attorney, Agent, or Firm*—Keil & Weinkauf

(57) ABSTRACT

The present invention provides cereal selective herbicidal compositions comprising a herbicidally acceptable carrier and/or surfactant and, as active ingredient, herbicidally effective amount of at least one 6-phenoxypyrid-2-ylcarboxamide of formula I and at least one additional herbicidal compound selected from the group consisting of flufenacet, cinidon-ethyl and carfentrazone-ethyl.

Also provided is a method for the control of undesirable plants such as *Setaria viridis, Alopecurus myosuroides, Poa annua, Stellaria media, Lamium purpureum, Galium aparine, Veronica hederaefolia, Papaver rhoeas* and *Matricaria inodora* which comprises applying to the plants or their locus a herbicidally effective amount of said compositions. The compositions have been found to possess synergistic properties.

37 Claims, No Drawings

SYNERGISTIC HERBICIDAL MIXTURES

This application claims benefit of appln. 60/194,383 filed Apr. 4, 2000 and appln. 60/231,631 filed Sep. 11, 2000.

Herbicidal 6-phenoxypyrid-2-ylcarboxamides such as those disclosed U.S. Pat. No. 5,294,597 display excellent herbicidal performance, in particular against broad-leaved weeds in crops such as cereal crops. However, when used as the sole active ingredient, the 6-phenoxypyrid-2-ylcarboxamides do not always achieve effective control of the full spectrum of weed species encountered in commercial agronomic applications, in conjunction with reliable selectivity for the crop species. Such gaps in the spectrum of control can be overcome by co-treatment with another herbicide known to be effective against the relevant weed species. The combined use of these 6-phenoxypyrid-2-ylcarboxamides with special further and other herbicides has been described in U.S. Pat. No. 5,674,807.

Therefore it is an object of this invention to provide further herbicidal combinations which exhibit a good herbicidal action exceeding the activity of one active ingredient alone, in particular in cereal crops.

It is another object of this invention to provide methodes for controlling undesired vegatation, in particular dicotyledonous weeds, using the herbicidal combinations. It is a further object of this invention to provide the method of use of the herbicidal combinations for controlling undesired vegetation, in particular in cereal crops, and in particular against dicotyledonous weeds.

We have found that this object is achieved by herbicidal compositions which comprise an agriculturally acceptable carrier and a herbicidally effective amount of a combination of at least one 6-phenoxypyrid-2-ylcarboxamide of formula I

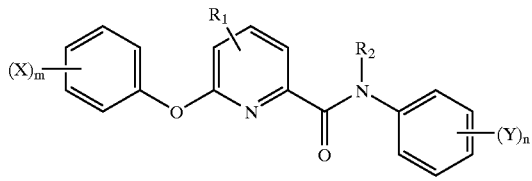

$R_1$ represents a hydrogen or halogen atom or an alkyl or alkoxy group;

$R_2$ represents a hydrogen atom or an alkyl group;

X each independently represents a halogen atom or an optionally substituted alkyl or alkoxy group or an alkenyloxy, cyano, carboxy, alkoxycarbonyl, (alkylthio)carbonyl, alkylcarbonyl, amido, alkylamido, dialkylamido, nitro, alkylthio, haloalkylthio, alkenylthio, alkynylthio, alkylsulphinyl, alkylsulphonyl, alkyloximinoalkyl or alkenyloximinoalkyl group;

m represents 0 or an integer from 1 to 5;

Y each independently represents a halogen atom or an alkyl, nitro, cyano, haloalkyl, alkoxy or haloalkoxy group;

n represents 0 or an integer from 1 to 5, and at least one additional herbicidal compound selected from the group consisting of flufenacet, cinidon-ethyl and carfentrazone-ethyl.

The present invention also provides a method for controlling undesirable plant species comprising application of said compositions. In the method of this invention, these compounds may be applied separately or together, in herbicidally effective amounts, and in the presence of a crop, preferably a cereal crop, such as wheat.

Although 6-phenoxypyrid-2-ylcarboxamides such as those disclosed in U.S. Pat. No. 5,294,597 display excellent herbicidal performance, when used as the sole active ingredient, they do not always achieve effective control of the full spectrum of weed species encountered in commercial agronomic applications, in conjunction with reliable selectivity for the crop species.

It has now been found that combinations comprising 6-phenoxypyrid-2-ylcarboxamide of formula I

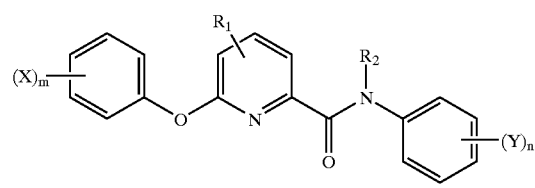

wherein $R_1$, $R_2$, X, Y, m and n are defined as above, with at least one additional herbicidal compound selected from the group of flufenacet, cinidon-ethyl or carfentrazone-ethyl provide synergistic control of troublesome broad-leaved weeds and annual grasses, especially such as *Setaria viridis, Alopecurus myosuroides, Poa annua, Stellaria media, Lamium purpureum, Galium aparine, Veronica hederaefolia, Papaver rhoeas* and *Matricaria inodora*. That is, application of the combination of the invention gives a mutual reinforcing action such that the application rates of the individual herbicidal component can be reduced and still the same herbicidal effect is achieved or, alternatively, the application of the combination of herbicidal components demonstrates a greater herbicidal effect than expected from the effect of the application of the individual herbicidal components when applied singly at the rate at which they are present in the combination (synergistic effect).

In the specification and claims, alkyl groups, unless otherwise specified, may be linear or branched and may contain up to 12, preferably 1 to 4, carbon atoms. The alkenyl or alkynyl portion of an alkynyloxy, alkenylthio or alkynylthio group, unless otherwise specified, may be linear or branched and may contain up to 12, preferably 2 to 4, carbon atoms. Examples of such groups are methyl, ethyl, propyl, vinyl, allyl, isopropyl, butyl, isobutyl and tertiary-butyl groups. The alkyl portion of a haloalkyl, haloalkoxy, alkylthio, haloalkylthio, alkoxy, alkoxycarbonyl, (alkylthio)carbonyl, alkylamido, dialkylamido, alkylsulfinyl or alkylsulfonyl group suitably has form 1 to 4 carbon atoms, preferably 1 or 2 carbon atoms. The number of carbon atoms in the alkyloximinoalkyl or alkenyloximinoalkyl groups is up to 6, preferably up to 4, e.g. 2-methoximinoethyl, 2-methoximinoproyl or 2-ethoximinopropyl.

"Halogen" means a fluorine, chlorine, bromine or iodine atom, preferably fluorine, chlorine or bromine. Haloalkyl, haloalkylthio and haloalkoxy are preferably mono-, di or trifluoroalkyl, -alkylthio and -alkoxy, especially trifluoromethyl, difluoromethoxy, trifluoromethylthio and trifluoromethoxy.

When any groups are designated as being optionally substituted, the substituent groups which are optionally present may be any of those customarily employed in the modification and/or development of pesticidal compounds and are especially substituents that maintain or enhance the herbicidal activity associated with the compounds of the present invention, or influence persistence of action, soil or plant penetration, or any other desirable property of such herbicidal compounds. There may be one or more of the same or different substituents present in each part of the molecules. In relation to moieties defined above as comprising optionally substituted alkyl- and alkoxy groups, specific examples of such substituents include phenyl, halogen atoms, nitro, cyano, hydroxyl, $C_{1-4}$-alkoxy, $C_{1-4}$haloalkoxy and $C_{1-4}$-alkoxycarbonyl groups.

A prefers embodiment of the invention provides herbicidal compositions which comprise an agriculturally acceptable carrier and a herbicidally effective amount of a combination of at least are 6-phenoxypyrid-2-ylcarboxamide of formula I and at least flufenacet as additional herbicidal compound.

A further preferred embodiment of the invention provides herbicidal compositions which comprise an agriculturally acceptable carrier and a herbicidally effective amount of a combination of at least one 6-phenoxypyrid-2-ylcarboxamide of formula I and at least carfentrazone-ethyl as additional herbicidal compound.

A further preferred embodiment of the invention provides herbicidal compositions which comprise an agriculturally acceptable carrier and a herbicidally effective amount of a combination of at least one 6-phenoxypyrid-2-ylcarboxamide of formula I and at least cinidon-ethyl.

Preferred compounds for use as 6-phenoxypyrid-2-ylcarboxamides according to the invention are compounds of formula I, wherein $R_1$ represents a hydrogen atom or a $C_{1-4}$-alkoxy group;

$R_2$ represents a hydrogen atom;

X represents a halogen atom or a $C_{1-4}$-haloalkyl group;

m represents an integer from 1 to 3, in particular 1;

Y represents preferably a halogen atom or a $C_{1-4}$-haloalkyl group; and n represents an integer from 1 to 3, in particular 1.

Especially preferred compounds for use as 6-phenoxypyrid-2-ylcarboxamides according to the invention are the compounds of formula IA,

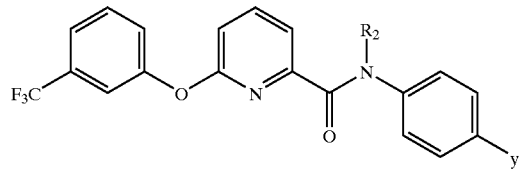

IA in particular N-(4-fluorophenyl)-6-(-3-trifluoromethylphenoxy)-pyrid-2-ylcarboxamide coded picolinafen.

A preferred embodiment of the present invention provides a herbicidal composition which comprises an agriculturally acceptable carrier and a herbicidally effective amount of a combination of picolinafen and flufenacet.

A further preferred embodiment of the present invention provides a herbicidal composition which comprises an agriculturally acceptable carrier and a herbicidally effective amount of a combination of picolinafen and cinidon-ethyl.

A further preferred embodiment of the present invention provides a herbicidal composition which comprises an agriculturally acceptable carrier and a herbicidally effective amount of a combination of picolinafen and carfentrazone-ethyl.

Flufenacet is the proposed common name of N-(4-fluorophenyl)-N-(1-methylethyl)-2-{[5-trifluoromethyl)-1, 3,4-thiadiazol-2-yl]oxy}acetamide, which is disclosed for example in U.S. Pat. No. 5,090,991.

Cinidon-ethyl is the common name of ethyl (Z)-2-chloro-3-[2-chloro-5-(1,3-dioxo-4,5,6,7-tetrahydroisoindol-2-yl)-phenyl]acrylate, which is disclosed for example by K. Grossmann, H. Schiffer, Pestic. Sci. (1999), 55(7), 687–695. CODEN: PSSCBG ISSN: 0031-613X.

Carfentrazone-ethyl is the common name of ethyl (RS)-2-chloro-3-[2-chloro-5-(4-difluoromethyl-4,5-dihydro-3-methyl-5-oxo-1H-1,2,4-triazol-1-yl)-4-fluorophenyl] propionate, which is reported by W. A. Van Saun et al, Proc Br. Crop. Prot. Conf., Weeds, 1993, 1, 19.

The pattern of persistence of the compounds of formula I is such that the combined treatment according to the present invention can be attained either by the application of a prepared mixture as defined above, or by time separated application of separate formulations. Hence, in another preferred embodiment, the present invention provides a method for controlling the growth of weeds at a crop locus which comprises applying to the locus a compound of formula I as defined above and a second component selected from the group consisting of flufenacet, cinidon-ethyl and carfentrazone-ethyl and mixtures thereof.

The treatment according to the invention may be used to control a broad spectrum of weed species in crops, particularly cereal crops such as in wheat, barley, rice and maize, by pre- or post-emergence treatment, including both early and late post-emergence. The combined use described above offers both foliar and residual activity.

By the term "pre-emergence application" is meant application to the soil in which the weed seeds or seedlings are present before emergence of the weeds above the surface of the soil. By the term "post-emergence application" is meant application to the aerial or exposed portions of the weeds which have emerged above the surface of the soil. It will be appreciated that application according to the method may be from pre- to post-weed emergence, and from pre-crop emergence to post-crop emergence. If one of the active ingredients or the composition of the active ingredients is less well tolerated by certain crop plants, application techniques may be employed in which the herbicidial composition is sprayed, with the aid of the spraying equipment, in such a way that the leaves of the sensitive crop plants come into as little contact as possible, if any, with ten active ingredient(s), while the latter reach the lleaves of undesired plants which grow underneath, or the naked surface (post directed, lay-by). By the term "foliar activity" is meant herbicidal activity obtained by application to the aerial or exposed portions of the weeds which have emerged above the surface of the soil. By the term "residual activity" is meant herbicidal activity obtained some time after application to the soil whereby seedlings present at the time of application or which germinate subsequent to application are controlled.

Weeds that may be controlled by the practice of the present invention include:

*Agrostis stolonifera*
*Alopecurus myosuroides*
*Anthemis arvensis*
*Apera spica-venti*
*Aphanes arvensis*
*Arenaria seryllifolia*
*Atriplex patula*
*Avena fatua*
*Bromus sterilis*
*Capsella bursa-pastoris*

-continued

Centaurea cyanus
Cerastes holosteoides
Chenopodium album
Chrysantemum segetum
Cirsium arvense
Eleusine indica
Euphorbia helioscopia
Fumaria officinalis
Galeopsis tetrahit
Galium aparine
Geranium dissectum
Lamium amplexicaule
Lamium purpureum
Legousia hybrida
Lolium perenne
Matricaria inodora
Matricaria matricoides
Montia perfoliata
Myosotis arvensis
Papaver rhoeas
Phalaris minor
Phalaris paradoxa
Poa annua
Poa trivialis
Polygonum aviculare
Polygonum convolvulus
Polygonum lapathifolium
Portulaca oleracea
Raphanus raphanistrum
Senecia vulgaris
Setaria viridis
Silene vulgaris
Spergula arvensis
Stellaria media
Thlaspi arvense
Veronica hederaefolia
Veronica persica
Viola arvensis The necessary application rate of active ingredient composition without formulation auxiliaries, depends on the composition of the plant stand, on the development stage of the plants, on the climatic conditions at the site of action, and on the application technique. In general, the application rate of the active ingedients together is from 0.001 to 10 kg a.I./ha; preferably from 0.001 to 3 kg ha, in particular 0.01 to 1 kg/ha. In another embodiment of the invention the application rate of the active ingredients together is from 0.01 to 10 kg a.i./ha.

The application rate of the compound of formula I is usually in the range of 5 to 500, preferably 7.5–200 grams of active ingredient (g a.i.) per hectare, with rates between 10–100 g a.i./ha often achieving satisfactory control and selectivity. The optimal rate for a specific application will depend on the crop(s) under cultivation and the predominant species of infesting weed, and readily may be determined by established biological tests known to those skilled in the art.

The selection of the herbicidally active second component will likewise be dependent on the crop/weed situation to be treated, and will be readily identifiable by those skilled in this area. The application rate for this second component is determined primarily by the chemical type of the component, since the intrinsic activity of different types of herbicide varies widely. In general, the preferred application rate of flufenacet is in the range of 7.5–400, preferably 10–200 g a.i./ha; the preferred application rate for cinidon-ethyl is in the range of 10–500, preferably 15–250 g/ha; the preferred application rate for carfentrazone-ethyl is in the range of 1–150, preferably 2.5–75 g/ha. The optimal rate for the second component will, however, depend on the crop(s) under cultivation and the level of weed infestation, and can readily be determined by established biological tests.

Naturally, with such a wide variation in application rate for the second component, the ratio of a formula I compound to a second component in the present invention will be determined predominantly by the choice of the second component. In general the compound of formula I and the second herbicide are employed in such weight ratios that the synergistiv effect is observed. The ratio (by weight) of compound of formula I to the second herbicidal compound is as a rule, from 1000:1 to 1:100, preferably from 100:1 to 1:20, in particular from 10:1 to 1:10.

In a preferred embodiment. The ratio (by weight) of compound of formula I to the second herbicidal compound is as a rule, from 100:1 to 1:100, preferably from 20:1 to 1:20, in particular from 10:1 to 1:10. The preferred formula I to second component ratio may vary, e.g., from about 5:1 to about 1:5.

In another prefered embodiment the ratio (by weight) of compound of formula I to the second herbicidial compound is as a rule from 1000:1 to 1:10, preferably from 100:1 to 1:5, in particular from 10:1 to 1:3,3.

Preferably the compound of formula I is picolinafen and the second compound is cinidon-ethyl.

The active compounds can be used in the form of a mixture of separate formulations, typically mixed with water prior to application (tank-mixtures), or as separate formulations applied individually within a certain time interval. Both active compounds can also be formulated together in a suitable ratio according to the present invention, together with usual carriers and/or additives known in the art.

Accordingly, the invention further provides a herbicidal composition which comprises as active ingredient, a herbicidally effective amount of at least one compound of formula I as defined above, and at least one compound selected from group consisting of flufenacet, cinidon-ethyl, carfentrazone-ethyl and one or more carriers. Another embodiment of the invention provides a herbicidal composition which comprises as active ingredient a herbicidally affective amount of at least one compound of formula I as defined above, and at least one compound selected from the group consisting of flufenacet, cinidon-ethyl and carfentrazone-ethyl, one or more carriers and at least one surfactant. A method of making such a composition is also provided which comprises bringing the mixture of the compound of formula I and the second component into association with the carrier(s) and if desired with the surfactant(s).

A composition according to the invention generally comprise approximately from 0.001% to 98% by weight (w/w) of active ingredients, preferably contains from 0.01% to 95% by weight (w/w), in particular from 0.5% to 95% by weight (w/w). The active ingredients are employed in a purity of 80% to 100%, preferably 90% to 100%, in particular 95% to 100% (according to NMR-Spectrum).

A carrier in a composition according to the invention is any material with which the active ingredient is formulated to facilitate application to the locus to be treated, which may for example be a plant, seed or soil, or to facilitate storage, transport or handling. A carrier may be a solid or a liquid, including material which is normally a gas but which has been compressed to form a liquid.

The compositions may be manufactured into e.g. emulsion concentrates, solutions, oil in water emulsions, wettable powders, soluble powders, suspension concentrates, dusts, granules, water dispersible granules, micro-capsules, gels and other formulation types by well-established procedures. These procedures include intensive mixing and/or milling of the active ingredients with other substances, such as fillers, solvents (liquid carriers), solid carriers, surface active compounds (surfactants), and optionally solid and/or liquid auxiliaries and/or adjuvants such as wetters, adhensives, dispersants or emulsifiers.

Granules, for example coated granules, impregnated granules and homogeneous granules, can be prepared by binding the active ingredient(s) and if desired other substances, such as surface active compounds, liquid auxiliaries and/or adjuvants, to the solid carrier.

Suitable liquid carriers (solvents) are essentially: mineral oil fractions of medium to high boiling point such as kerosine and diesel oil, furthermore coal tar oils and oils of vegetable or animal origin; aliphatic, cyclic and aromatic hydrocarbons, for example cyclohexane, parafins, tetrahydronaphthalene, alkylated naphthalenes and their derivatives, alkylated benzenes and their derivated (such as Solvesso® 200); phthalic acid esters, such as dibutyl or dioctyl phthalate; alcohols ad glycols as well as their ethers and esters, e.g. methanol, ethanol, propanol, butanol, cyclohexanol, ethylene glycol mono- and dimethyl ether; ketones such as cyclohexenone; strongly polar solvents, for examples amines such as N-methyl pyrrolidone, N-octylpyrrolidone and N-cyclohexylpyrrolidone, or lactones such as γ-butyrolactone; epoxidized plant oil esters such as methylated coconut or soybean oil ester; and water. Mixtures of different liquid carries are often suitable.

Surfactants may be nonionic, anionic, cationic or zwitterionic substances with good dispersing, emulsifying and wetting properties depending on the nature of the compound according to general formula I and/or the additional herbicidal compound selected from the group consisting flufenacet, cinidon-ethyl and carfentrazone-ethyl to be formulated. Surfactants may also mean mixtures of individual surfactants.

Solid carries are essentially:

mineral earth such as silicas, silica gels, silicates, talc, kaolin, montmorillonite, attapulgite, pumice, sepiolite, bentonite, limestone, lime, chalk, bole, loes, clay, dolomite, diatomaceous earth, calcite, calcium sulfate, magnesium sulfate, magnesium sulfate, magnesium oxide, sand, ground plastics, ferilizers such as ammonium sulfate, ammonium phosphat, ammonium nitrate, ureas, and crushed products of vegetable origin such as cereal meal, tree bark meal, wood meal and nutshell meal, cellulose powders, or other solid carriers.

Suitable sufactants are the alkali metal salts, alkaline earth metal salts and ammonium salts of aromatic sulfonic acids, for example lignin-, phenol-, naphthalene- and dibutylnaphthalene-sulfonic acid, and of fatty acids, of alkyl- and alkylaryl-sulfonates, of alkyl, lauryl ether and fatty alcohol sulfates, and salts of sulfated hexa-, hepta- and octadecanols and of fatty alcohol glycol ether, and condensates of sulfonated naphthalene and its derivatives with formaldehyde, condensates of naphthalene or of naphthalenesulfonic acids with phenol and formaldehyde, polyoxyethylene octylphenol ether, ethoxylated isooctyl-, octyl- or nonylphenol, alkylphenyl and tributylphenyl polyglycol ethers, alkylaryl polyether alcohols, isotridecyl alcohol, fatty alcohol/ethylene oxide condensates, ethoxylated castor oil, polyoxyethylene alkyl ethers or polyoxypropylene alkyl ethers, lauryl alcohol polyglycol ether acetate, sorbitol esters, lignin-sulfite waste liquors or methylcellulose.

Pesticidal compositions are often formulated and transported in a concentrated form which is subsequently diluted by the user before application. The presence of small amounts of a surfactant facilitate this process of dilution. Thus, preferably a composition according to the invention comprises if desires at least one surfactant. For example, the composition may contain one or more carriers and at least one surfactant.

The compositions of the invention may for example be formulated as wettable powders, water dispersible granules, dusts, granules, solutions, emulsifiable concentrates, emulsions, suspension concentrates and aerosols. Wettable powders usually contain 5 to 90% w/w of active ingredient and usually contain in addition to solid inert carrier, 3 to 10% w/w of dispersing and wetting agents and, where necessary, 0 to 10% w/w of stabilizer(s) and/or other additives such as penetrants or stickers. Dusts are usually formulated as a dust concentrate having a similar composition to that of a wettable powder but without a dispersant, and may be diluted in the field with further solid carrier to give a composition usually containing 0.5 to 10% w/w of active ingredient. Water dispersible granules and granules are usually prepared to have a size between 0.15 mm and 2.0 mm and may be manufactured by a variety of techniques. Generally, these types of granules will contain 0.5 to 90% w/w active ingredient and 0 to 20% w/w of additives such as stabilizer, surfactants, slow release modifiers and binding agents. The so-called "dry flowables" consist of relatively small granules having a relatively high concentration of active ingredient. Emulsifiable concentrates usually contain, in addition to a solvent or a mixture of solvents, 1 to 80% w/v active ingredient, 2 to 20% w/v emulsifiers and 0 to 20% w/v of other additives such as stabilizers, penetrants and corrosion inhibitors. Suspension concentrates are usually milled so as to obtain a stable, non-sedimenting flowable product and usually contain 5 to 75% w/v active ingredient, 0.5 to 15% w/v of dispersing agents, 0.1 to 10% w/v of suspending agents such as protective colloids and thixotropic agents, 0 to 10% w/v of other additives such as defoamers, corrosion inhibitors, stabilizers, penetrants and retention enhancers (stickers), and water or an organic liquid in which the active ingredient is substantially insoluble; certain organic solids or inorganic salts may be present dissolved in the formulation to assist in preventing sedimentation and crystalization or as antifreeze agents for water.

The forms of application of the compositions according to the invention depend on the intended purposes; in any case, they should guarantee as fine as possible a distribution of the active ingredients. They can be applied, for example, in the form of directly sprayable aqueous solutions, powders, suspensions, also highly-concentrated aqueous, oily or other suspensions or dispersions, emulsions, oil dispersions, pastes, dusts, materials for spreading or granules, by spraying, atomizing, dusting or pouring.

Aqueous use forms can be prepared from emulsion concentrates, suspensions, pastes, wettable powders or water-dispersible granules by adding water. To prepare emulsions, pastes or oil dispersions, the herbicidally active ingredients as such or dissolved in an oil or solvent, can be homogenized in water by means of wetters, adhesives, dispersants or emulsifiers.

Alternatively, concentrates which consist of herbicidally active ingredients, wetter, adhesive, dispersant or emulsifier and, if appropriate solvent or oil may be prepared, and such concentrates are suitable for dilution with water.

Aqueous dispersions and emulsions, for example compositions obtained by diluting the formulated product according to the invention with water, also lie within the scope of the invention.

Of particular interest in enhancing the duration of the protective activity of the compounds of this invention is the use of a carrier which will provide slow release of the pesticidal compounds into the environment of a plant which is to be protected.

The biological activity of the active ingredient can also be increased by including an adjuvant in the spray dilution. An adjuvant is defined here as a substance which can increase the biological activity of an active ingredient but is not itself significantly biologically active. The adjuvant can either be included in the formulation as a coformulant or carrier, or can be added to the spray tank together with the formulation containing the active ingredient.

As a commodity the compositions may preferably be in a concentrated form whereas the end user generally employs diluted compositions. The compositions may be diluted to a concentration down to 0.001% of active ingredient, usually the formulation comprise approximately from 0.001 to 98% by weight, preferably 0.01 to 95% by weight, of active ingredients. The doses usually are in the range from 0.01 to 10 kg a.i./ha.

EXAMPLES OF FORMULATIONS ACCORDING TO THE INVENTION ARE

Emulsion Concentrate (EC)

| Active Ingredient | Picolinafen + flufenacet (1:2) | 30% (w/v) |
|---|---|---|
| Emulsifier(s) | Atlox ® 4856 B/Atlox ® 4858 B[1] (mixture containing calcium alkyl aryl sulfonate, fatty alcohol ethoxylates and light aromatics | 5% (w/v) |
| Solvent | Shellsol ® A[2] (mixture of $C_9$–$C_{10}$ aromatic hydrocarbons) | to 1000 ml |

Suspension Concentrate (SC)

| Active Ingredient | Picolinafen + carfentrazone-ethyl (4:1) | 50% (w/v) |
|---|---|---|
| Dispersing agent | Soprophor ® FL[3] (polyoxyethylene polyaryl phenyl ether phosphate amine salt) | 3% (w/v) |
| Antifoaming agent | Rhodorsil ® 422[3] (nonionic aqueous emulsion of polydimethylsiloxanes) | 0.2% (w/v) |
| Structure agent | Kelzan ® S[4] (Xanthan gum) | 0.2% (w/v) |
| Antifreezing agent | Propylene glycol | 5% (w/v) |
| Biocidal agent | Proxel ®[5] (aqueous dipropylene glycol solution containing 20% 1,2-benisothiazolin-3-one) | 0.1% (w/v) |
| Water | | to 1000 ml |

Wettable Powder (WP)

| Active Ingredient | Picolinafen + flufenacet (1:2) | 60% (w/w) |
|---|---|---|
| Wetting agent | Atlox ® 4995[1] (polyoxyethylene alkyl ether) | 2% (w/w) |
| Dispersing agent | Witcosperse ® D-60[6] (mixture of sodium salts of condensed naphthalene sulfonic acid and alkylarylpolyoxy acetates | 3% (w/w) |
| Carrier/Filler | Kaolin | 35% (w/w) |

Water Dispersible Granules (WG)

| Active Ingredient | Picolinafen + carfentrazone-ethyl (4:1) | 50% (w/w) |
|---|---|---|
| Dispersing/Binding agent | Witcosperse ® D-450[6] (mixture of sodium salts of condensed naphthalene sulfonic acid and alkyl sulfonates) | 8% (w/w) |
| Wetting agent | Morwet ® EFW[6] (formaldehyde condensation product) | 2% (w/w) |
| Antifoaming agent | Rhodorsil ® EP 6703[3] (encapsulated silicone) | 1% (w/w) |
| Disintegrant | Agrimer ® ATF[7] (cross-linked homopolymer of N-vinyl-2-pyrrolidone) | 2% (w/w) |
| Carrier/Filler | Kaolin | 35% (w/w) |

1) commercially available from ICI Surfactants
2) commercially available from Deutsche Shell AG
3) commercially available from Rhône-Poulenc
4) commercially available from Kelco Co.
5) commercially available from Zeneca
6) commercially available from Witco
7) commercially available from International Speciality Products The compositions of this invention can also comprise other compounds having biological activity, e.g. compounds having similar or complementary pesticidal activity or compounds having plant growth regulating, fungicidal, or insecticidal or antibacterial activity. These mixtures of pesticides can have a broader spectrum of activity than the synergistic composition according to this invention alone. Also of interest is the mixability with mineral salt solutions, which are employed for treating nutritional and trace element deficiencies. Nonphytotoxic oils and oil concentrates may also be added.

The following examples illustrate specific embodiments of the present invention; however, the invention is not limited to the embodiments so illustrated, but includes the entire scope of the appended claims.

For a more clear understanding of the invention, specific examples thereof are set forth below. These examples are merely illustrative, and are not to be understood as limiting the scope and underlying principles of the invention in any way.

In the following examples, synergism for two-way combinations is determined by the Colby[1] method, i.e. the expected (or predicted) response of the combination is calculated by taking the product of the observed response for each individual component of the combination when applied alone divided by 100 and subtracting this value from the sum of the observed response for each component when applied alone. Synergism of the combination is then determined by comparing the observed response of the combination to the expected (or predicted) response as calculated from the observed responses of each individual component alone. If the observed response of the combination is greater than the expected (or predicted) response then the combination is said to be synergistic and falls within the definition of synergistic effect as previously defined.

[1] Colby, S. R., Weeds, 1967(15), p. 20–22

The foregoing is illustrated mathematically below, wherein a two-way combination, $C_2$, is composed of component X plus component Y and Obs. designates the observed response of the combination $C_2$.

Postemergence Herbicidal Greenhouse Evaluations

Test Serie A

Plant seeds are sown in pots containing a loamy sand soil (0.5 l). The herbicides are applied as single treatments, or in a combination comprising a compound of formula I and a second compound as defined above, after emergence of weeds and crop. The herbicidal performance is assessed as percent damage in comparison to the untreated control plants. The assessment is done 21 days after the treatment. Wheat and barley are treated at the 3–4 leaf stage, the broad-leaf weeds at the 2–4 leaf stage and annual grasses at the 2–3 leaf stage.

$$(X + Y) - \frac{XY}{100} = \text{Expected response (Exp.)}$$

*Synergism≈Obs.>Exp.*

For the compound of formula I picolinafen is employed. The second component has application rates (and hence component ratios) chosen to be appropriate to the established activity level of that component.

The following abbreviations have been used in the tables:

EXP is the expected response by means of the Colby formula.

OBS is the observed response.

The damage caused by the chemicals was assessed with reference to a scale from 0 to 100% in comparison with the untreated control plants. 0 means no damage and 100 means compete destruction of the plants.

Table I gives the results of the postemergence herbicidal activity of piclonafen/flufenacet combinations on various weed species. As can be seen from the data shown in Table I the application of a combination of picolinafen plus flufenacet gives significantly greater weed control than that which could be predicted from the weed control resulting from the application of either picolinafen alone or flufenacet alone. Crop tolerance (wheat and barley) is excellent for all treatments.

Table II gives the results of the postemergence herbicidal activity of piclonafen/carfentrazone-ethyl combinations on Stellaria media. As can be seen from the data shown in Table II the application of a combination of picolinafen plus carfentrazone ethyl gives significantly greater weed control than that which could be predicted from the weed control resulting from the application of either picolinafen alone or carfentrazone-ethyl alone. Crop tolerance (wheat and barley) is excellent for all treatments.

TABLE I

Evaluation of the Postemergence Herbicidal Activity of Picolinafen/Flufenacet Combinations

| Weed Species | Picolinafen (g/ha) | Flufenacet (g/ha) | % Control EXP | % Control OBS |
|---|---|---|---|---|
| *Galium aparine* | 15 | 0 | — | 78 |
|  | 0 | 15 | — | 40 |
|  | 0 | 30 | — | 55 |
|  | 15 | 15 | 87 | 96 |
|  | 15 | 30 | 90 | 99 |
| *Stellaria media* | 15 | 0 | — | 53 |
|  | 30 | 0 | — | 73 |
|  | 0 | 30 | — | 0 |

TABLE I-continued

Evaluation of the Postemergence Herbicidal Activity of Picolinafen/Flufenacet Combinations

| Weed Species | Picolinafen (g/ha) | Flufenacet (g/ha) | % Control EXP | % Control OBS |
|---|---|---|---|---|
|  | 0 | 60 | — | 0 |
|  | 0 | 120 | — | 0 |
|  | 15 | 15 | 87 | 96 |
|  | 15 | 30 | 53 | 70 |
|  | 15 | 60 | 53 | 70 |
|  | 15 | 120 | 73 | 89 |
|  | 30 | 60 | 73 | 89 |
|  | 30 | 120 | 73 | 92 |
| *Alopecuris myosuroides* | 30 | 0 | — | 20 |
|  | 60 | 0 | — | 43 |
|  | 120 | 0 | — | 60 |
|  | 0 | 15 | — | 75 |
|  | 30 | 15 | 80 | 94 |
|  | 60 | 15 | 86 | 95 |
|  | 120 | 15 | 90 | 95 |
| *Papaver rhoeas* | 30 | 0 | — | 15 |
|  | 60 | 0 | — | 35 |
|  | 0 | 15 | — | 0 |
|  | 0 | 30 | — | 0 |
|  | 0 | 120 | — | 18 |
|  | 30 | 15 | 15 | 35 |
|  | 30 | 30 | 15 | 35 |
|  | 60 | 15 | 35 | 50 |
|  | 60 | 30 | 35 | 55 |
|  | 60 | 120 | 43 | 63 |
| *Lamium purpurium* | 30 | 0 | — | 15 |
|  | 0 | 120 | — | 18 |
|  | 30 | 120 | 30 | 58 |

TABLE II

Evaluation of the Postemergence Herbicidal Activity of Picolinafen/Carfentrazone-ethyl Combinations on *Stellaria media*

| Picolinafen (g/ha) | Carfentrazone-ethyl (g/ha) | % Control EXP | % Control OBS |
|---|---|---|---|
| 30 | 0 | — | 37 |
| 60 | 0 | — | 45 |
| 120 | 0 | — | 72 |
| 0 | 3.75 | — | 0 |
| 0 | 7.50 | — | 0 |
| 0 | 15 | — | 0 |
| 0 | 30 | — | 0 |
| 30 | 15 | 37 | 57 |
| 30 | 30 | 37 | 85 |
| 60 | 3.75 | 45 | 75 |
| 60 | 7.50 | 45 | 91 |
| 60 | 15 | 45 | 67 |
| 60 | 30 | 45 | 85 |
| 120 | 15 | 72 | 80 |
| 120 | 30 | 72 | 91 |

Test Serie B

For the post-emergence treatment, the test plants were first grown to a height of 3 to 20 cm, depending on the growth habit, and only then treated. The herbicides were suspended or emulsified in water as the vehicle and sprayed with the aid of finely distributing nozzles.

Cinidon-ethyl was formulated as a 20% by weight emulsion concentrate and employed in the spray mixture with addition of that amount of solvent system with which the active ingredient had been applied at the application rates shown in the tables.

Picolinofen was formulated as a 10% by weight emulsion concentrate and empolyed in the spray mixture with addition of that amount of solvent system with which the active ingredient had been applied at the rates shown in the tables.

The test period extended over 14 days. During this time, the plants were attended, and their responses to the treatments with active ingredients were recorded (Tables III and IV).

TABLE III

Evaluation of the Postemergence Herbicidal Activity of Picolinafen/Cinidon-ethyl Combinations in spring wheat

| Weed Species (growth stage 14) | Picolinafen (g/ha) | Cinidon-ethyl (g/ha) | % Control EXP | % Control OBS |
|---|---|---|---|---|
| Anthimis mixta | 50 | — | — | 10 |
| | — | 50 | — | 52 |
| | 50 | 50 | 57 | 68 |
| Veronica persicaria | 50 | — | — | 10 |
| | — | 50 | — | 50 |
| | 50 | 50 | 55 | 63 |

TABLE IV

Evaluation of the Postemergence Herbicidal Activity of Picolinafen/Cinidon-ethyl Combinations in spring barley

| Weed Species (growth stage 22) | Picolinafen (g/ha) | Cinidon-ethyl (g/ha) | % Control EXP | % Control OBS |
|---|---|---|---|---|
| Stellaria media | 50 | — | — | 10 |
| | — | 50 | — | 23 |
| | 50 | 50 | 31 | 47 |

What is claimed is:

1. A herbicidal composition which comprises an agriculturally acceptable carrier and a herbicidally effective amount of a combination of at least one 6-phenoxypyrid-2-ylcarboxamide of formula I

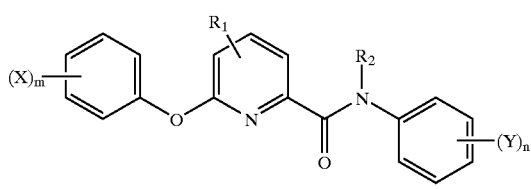

wherein
$R_1$ represents a hydrogen or halogen atom or an alkyl or alkoxy group;
$R_2$ represents a hydrogen atom or an alkyl group;
X each independently represents a halogen atom or an optionally substituted alkyl or alkoxy group or, an alkenyloxy, cyano, carboxy, alkoxycarbonyl, (alkylthio)carbonyl, alkylcarbonyl, amido, alkylamido, dialkylamido, nitro, alkylthio, haloalkylthio, alkenylthio, alkynylthio, akylsulphinyl, alkylsulphonyl, alkyloximinoalkyl or alkenyloximinoalkyl group;
m represents 0 or an integer from 1 to 5;
Y each independently represents a halogen atom or an alkyl, nitro, cyano, haloalkyl, alkoxy or haloalkoxy group;
n represents 0 or an integer from 1 to 5; and at least one additional herbicidal compound selected from the group consisting of flufenacet, cinidon-ethyl and carfentrazone-ethyl.

2. The composition according to claim 1 wherein the 6-phenoxypyrid-2-ylcarboxamide has the formula IA

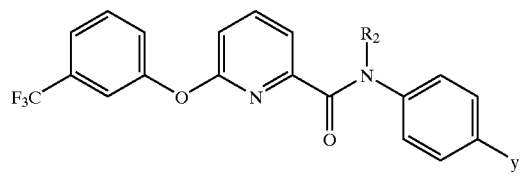

wherein $R^2$ and Y are as defined in claim 1.

3. The composition according to claim 2 wherein the 6-phenoxypyrid-2-ylcarboxamide is picolinafen.

4. The composition according to claim 3 wherein said additional herbicidal compound is flufenacet.

5. The composition according to claim 3 wherein said additional herbicidal compound is cinidon-ethyl.

6. The composition according to claim 3 wherein said additional herbicidal compound is carfentrazone-ethyl.

7. The composition according to claim 1 wherein said herbicidal composition comprises at least one surfactant.

8. The composition according to claim 7 wherein the 6-phenoxypyrid-2-ylcarboxamide is picolinafen and said additional herbicidal compound is cinidon-ethyl.

9. The composition according to claim 1 wherein the ratio (by weight) of the 6-phenoxypyrid-2-ylcarboxamide of formula I to said additional herbicidal compound is from 1000:1 to 1:200.

10. The composition according to claim 9 wherein the ratio (by weight) of the 6-phenoxypyrid-2-ylcarboxamide of formula I to said additional herbicidal compound is from 10:1 to 1:200.

11. The composition according to claim 9 wherein the ratio (by weight) of the 6-phenoxypyrid-2-ylcarboxamide of formula I to said additional herbicidal compound is from 1:1 to 1:80.

12. The composition according to claim 6 wherein the ratio (by weight) of picolinafen to said additional herbicidal compound cinidon-ethyl is 100:1 to 1:5.

13. The composition according to claim 6 wherein the ratio (by weight) of picolinafen to said additional herbicidal compound cinidon-ethyl is 10:1 to 1:3,3.

14. A method for the control of undesirable plants which comprises applying to the locus of said plants or to the foliage or stems or seeds of said plants a herbicidally effective amount of at least one 6-phenoxypyrid-2-ylcarboxamide of formula I

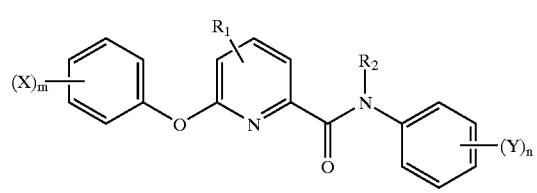

wherein $R^1$, $R^2$, X, Y, m and n are as defined in claim 1 and at least one additional herbicidal compound selected from the group consisting of flufenacet, cinidon-ethyl and carfentrazone-ethyl.

15. The method according to claim 14 where the 6-phenoxypyrid-2-ylcarboxamide has the formula IA

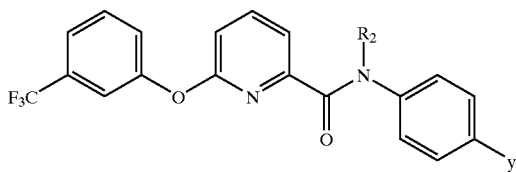

IA wherein $R^2$ and Y are as defined in claim 1.

16. The method according to claim 15 wherein the 6-phenoxypyrid-2-ylcarboxamide is picolinafen.

17. The method according to claim 16 wherein said additional herbicidal compound is flufenacet.

18. The method according to claim 16 wherein said additional herbicidal compound is cinidon-ethyl.

19. The method according to claim 16 wherein said additional herbicidal compound is carfentrazone-ethyl.

20. The method according to claim 18 wherein the herbicidal composition comprises at least one surfactant.

21. The method according to claim 18 which comprises applying picolinafen and cinidon-ethyl—simultaneously or in succession—before, during or after emergence of the undesired plants.

22. The method according to claim 14, wherein the phenoxypyrid-2-ylcarboxamide and the additional herbicidal compound are applied together in a single formulation.

23. The method according to claim 14, wherein the phenoxypyrid-2-ylcarboxamide and the additional herbicidal compound are applied in separate formulations.

24. The method according to claim 18 wherein picolinafen and cinidon-ethyl are applied together in a single fomulation.

25. The method according to claim 18 wherein picolinafen and cinidon-ethyl are applied in seperate formulations.

26. The method according to claim 14 wherein the phenoxypyrid-2-ylcarboxamide and the additional herbicidal compound are applied in the presence of a cereal crop plant, crop seed or other crop propagating organ.

27. The method according to claim 26 wherein the cereal crop is corn, wheat or rice.

28. The method according to claim 26 wherein the cereal crop is wheat.

29. A method of combating *Alopecurus myosuroides, Lolium perenne, Setaria viridis, Stellaria media, Veronica persica, Galium aparine, Apera spica-venti* and/or *Lamium purpureum* at a locus which comprises applying to the locus a herbicidally effective amount of a composition of claim 1.

30. A method for the control of dicotyledonous weeds in cereal crops which comprises applying picolinafen and cinidon-ethyl—simultaneously or in succession—before, during or after the emergence of the dicotyledonous weeds.

31. A method for the control of undesirable plants which comprises treating the leaves of the undesired plants with picolinafen and cinidon-ethyl, either simultaneously or in succession.

32. A method for the control of dicotyledonous weeds which comprises treating the leaves of the dicotyledonous weeds with picolonafen and cinidon-ethyl, either simultaneously or in succession.

33. Method of using the composition as claimed in claim 1 comprising applying the composition to undesired vegetation.

34. Method of using the composition according to claim 32 wherein the composition comprises as 6-phenoxypyrid-2-ylcarboxamide picolinafen and as additional herbicidal compound cinidon-ethyl.

35. Method of using the composition according to claim 32 wherein the composition comprises as 6-phenoxypyrid-2-ylcarboxamide picolinafen and as additional herbicidal compound cinidon-ethyl for controlling undesired vegetation in cereal crops.

36. Method of using the composition according to claim 32 wherein the composition comprises as 6-phenoxypyrid-2-ylcarboxamide picolinafen and as additional herbicidal compound cinidon-ethyl for controlling dicotyledonous weeds.

37. Herbicidal agent which is prepared in two parts, the one part comprising picolinafen and an agriculturally acceptable carrier and the other one comprising cinidon-ethyl and an agriculturally acceptable carrier.

* * * * *